(12) United States Patent
Dhawan et al.

(10) Patent No.: US 8,420,862 B2
(45) Date of Patent: *Apr. 16, 2013

(54) PROCESS FOR THE PREPARATION OF HIGHLY PURE MONOMERS FOR POLYBENZIMIDAZOLE MATERIALS

(75) Inventors: Rajiv Dhawan, Wilmington, DE (US); Joachim C. Ritter, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 537 days.

This patent is subject to a terminal disclaimer.

(21) Appl. No.: 12/634,745

(22) Filed: Dec. 10, 2009

(65) Prior Publication Data

US 2010/0160596 A1 Jun. 24, 2010

Related U.S. Application Data

(60) Provisional application No. 61/138,626, filed on Dec. 18, 2008.

(51) Int. Cl.
*C07C 211/00* (2006.01)
(52) U.S. Cl.
USPC ........... 564/306; 528/331; 562/480; 564/305; 564/415; 564/441
(58) Field of Classification Search ........... 528/331; 564/305, 306, 415, 441; 562/480
See application file for complete search history.

(56) References Cited

U.S. PATENT DOCUMENTS

| 3,476,590 A | 11/1969 | Rabilloud |
| 3,783,137 A | 1/1974 | Gerber |
| 5,142,021 A | 8/1992 | Lysenko et al. |
| 6,040,478 A | 3/2000 | Sikkema et al. |
| 6,169,165 B1 * | 1/2001 | Kubota et al. ................. 528/486 |
| 6,617,414 B2 * | 9/2003 | Hotta et al. ................... 528/184 |
| 8,143,450 B1 * | 3/2012 | Ritter et al. ................... 564/306 |
| 8,163,961 B2 * | 4/2012 | Dhawan et al. ............... 564/441 |
| 8,188,316 B2 * | 5/2012 | Dhawan et al. ............... 564/441 |

FOREIGN PATENT DOCUMENTS

| JP | 2003292476 | 10/2003 |
| JP | 2005330470 | 12/2005 |
| JP | 2005330471 | 12/2005 |

OTHER PUBLICATIONS

Dhawan et al., U.S. Appl. No. 12/634,757, filed Dec. 10, 2009.
Dhawan et al., U.S. Appl. No. 12/634,799, filed Feb. 22, 2010.
Dhawan et al., U.S. Appl. No. 12/634,825, filed Dec. 10, 2009.
Ritter et al. U.S. Appl. No. 12/634,730, filed Dec. 10, 2009, (Was U.S. Appl. No. 61/138,602).

* cited by examiner

*Primary Examiner* — Gregory Listvoyb
(74) *Attorney, Agent, or Firm* — Kevin S. Dobson

(57) ABSTRACT

Highly pure 2,3,5,6-tetraaminotoluene species are produced by chemically reducing undesirable oxidation byproducts. The 2,3,5,6-tetraaminotoluene species are then used in the manufacture of superior high-performance polybenzimidazole polymers.

3 Claims, 3 Drawing Sheets

PROCESS FOR THE PREPARATION OF HIGHLY PURE MONOMERS FOR POLYBENZIMIDAZOLE MATERIALS

This application claims priority under 35 U.S.C. §119(e) from, and claims the benefit of, U.S. Provisional Application No. 61/138,626, filed Dec. 18, 2008, which is by this reference incorporated in its entirety as a part hereof for all purposes.

TECHNICAL FIELD

The disclosure relates to methods of making highly pure 2,3,5,6-tetraaminotoluene species, which are then used in the manufacture of high-performance polybenzimidazole polymers.

BACKGROUND

The synthesis of preferred polybenzimidazole based high performance fibers requires the selective polymerization of 2,3,5,6-tetraaminotoluene ("TAT", also known as 3-methyl-2,3,5,6-tetraaminobenzene) with various substituted and unsubstituted aromatic diacids, such as 2,5-dihydroxyterephthalic acid ("DHTA").

TAT (Formula I)

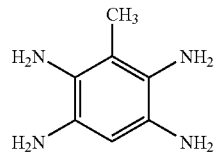

has been mentioned in the literature (e.g., U.S. Pat. Nos. 3,476,590 and 3,783,137) as a comonomer in the synthesis of polybenzarenazole polymers. TAT can be used as a crosslinking comonomer using radical induced crosslinking at the methyl group. For example, in Japanese Patent Application 2005-330470 A, TAT is used as a crosslinking comonomer in the synthesis of a polybenzimidazole polymer for film applications. However, none of these references discloses a source or synthesis for TAT.

A method for preparing the 2,3,5,6-tetraaminotoluene for use in step (a) by hydrogenating 2-methyl-1,3-diamino-4,6-dinitrobenzene (II)

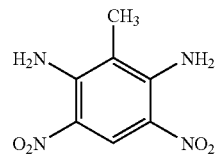

is disclosed in co-pending U.S. Provisional Application 61/138,602, which is by this reference incorporated in its entirety as a part hereof for all purpose.

A 1:1 complex formed between TAT and the aromatic diacid is the monomer of choice for the production of a high molecular weight polymer for high strength fiber. The ratio of diacid to tetraamine must be as close to 1:1 as possible to achieve high molecular weight. However, the oxidative instability of TAT species, including TAT, TAT salts such as TAT-.nHX (n=0-4, X=Cl, Br), and the complex of TAT with aromatic diacid, during the reaction and handling processes leads to the formation of oxidation byproducts, such as 2-methyl-3,6-diiminocyclohexa-1,4-diene-1,4-diamine (Formula III),

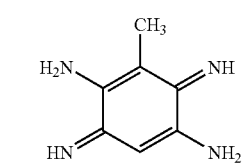

phenazine-1,6-dimethyl-2,3,7,8-tetraamine (Formula IV) and phenazine-1,9-dimethyl-2,3,7,8-tetraamine (Formula V):

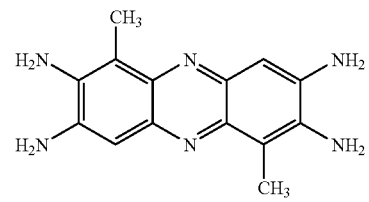

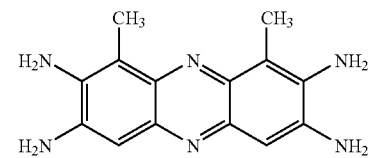

in the manner as shown by the reaction schemes set forth below:

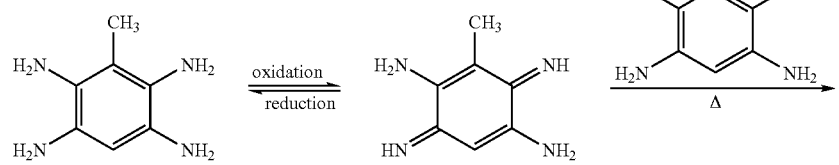

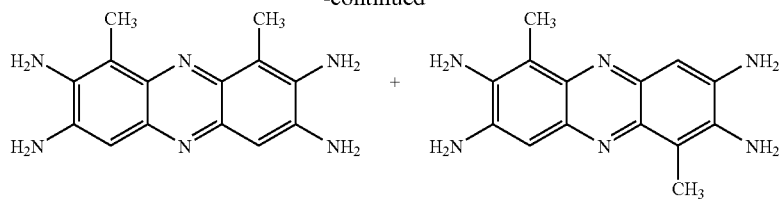

As a consequence, the TAT:aromatic diacid ratio is far enough from 1:1 that polymer produced from it does not have high enough molecular weight for it to be suitable for the production of high-performance fiber.

In U.S. Pat. No. 5,142,021, Lysenko et al. claim a process for synthesizing a polybenzazole polymer comprising the step of reacting monomers (for example, terephthalic acid with 4,6-diaminoresorcinol, 2,5-diaminohydroquinone, 2,5-diamino-1,4-dithiobenzene or acid salts thereof) in a non-oxidizing dehydrating solvent acid solution that contains polyphosphoric acid and/or methanesulfonic acid, in the presence of a reducing agent present in a quantity of at least 0.5 weight percent of the quantity of monomers. The reducing agent is not added until the oligomerization step of the polymerization process.

However, it is important to prevent or reverse oxidation prior to the polymerization step in order to avoid side reactions causing an imbalance in the ratio of the co-monomers. It is also desirable to add as little Sn to the polymer as possible to avoid Sn contamination of the final polymer product and costly purification.

There thus remains a need for a high-yield method to prepare highly pure 2,3,5,6-tetraaminotoluene species without significant amounts of oxidation byproducts and contamination of the polymer with reducing agents or costly processes for the removal of reducing agents.

SUMMARY

In one embodiment, this invention provides an aqueous mixture comprising at least one 2,3,5,6-tetraaminotoluene species in suspension or in solution, and a reducing agent that reduces oxidation byproducts at the pH of the aqueous mixture.

In another embodiment, this invention provides a process for preparing 2,3,5,6-tetraaminotoluene salt, by (a) providing a 2,3,5,6-tetraaminotoluene feed in the form of an aqueous solution or an aqueous suspension; (b) contacting the 2,3,5,6-tetraaminotoluene feed with an acid feed to form a reaction mixture at a temperature between about 10 and about 100° C. to produce 2,3,5,6-tetraaminotoluene salt; and (c) cooling the reaction mixture to precipitate the 2,3,5,6-tetraaminotoluene salt; wherein at least one of the feeds and/or the reaction mixture further comprises a reducing agent that reduces oxidation byproducts at the pH of the aqueous mixture.

In another embodiment, this invention provides a process for preparing a complex of 2,3,5,6-tetraaminotoluene and the aromatic diacid XYTA, wherein the complex is generally described by Formula VI

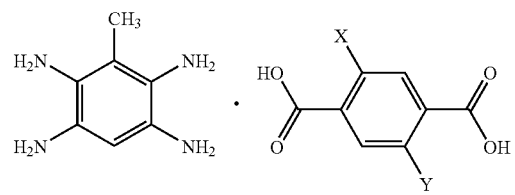

wherein X and Y are each independently selected from the group consisting of H, OH, SH, methyl, ethyl, F, Cl, and Br; comprising the sequential steps under exclusion of oxygen; by (a) providing a 2,3,5,6-tetraaminotoluene feed in the form of an aqueous solution or aqueous suspension; (b) forming a reaction mixture combining the 2,3,5,6-tetraaminotoluene feed with the following feeds: (i) 0 to 5 equivalents of an acid, (ii) 0 to 5 equivalents of an organic base or an inorganic base, (iii) optionally, a buffer solution, and (iv) an XYTA source selected from XYTA and $M_2$XYTA (Formula VII)

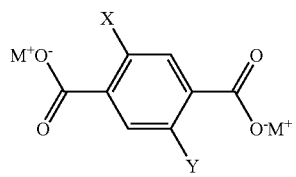

wherein M is K or Na, and wherein the molar ratio of XYTA to the 2,3,5,6-tetraaminotoluene salt is from 1:1 to 1:1.1; thereby adjusting the pH of the mixture to between about 3 and about 10 and thereby producing and precipitating the complex generally described by Formula (VI); and (c) cooling, filtering, and washing the precipitated complex; wherein at least one of the feeds and/or the reaction mixture further comprises a reducing agent that reduces oxidation byproducts at the pH of the aqueous mixture.

In another embodiment, this invention provides a process for preparing a polybenzimidazole polymer comprising polymerizing a complex of 2,3,5,6-tetraaminotoluene and the aromatic diacid XYTA, wherein the complex is generally described by Formula VI

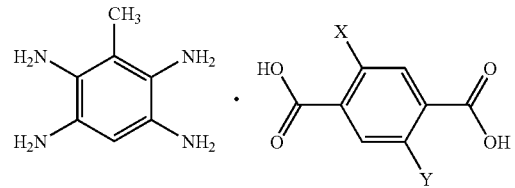

wherein X and Y are each independently selected from the group consisting of H, OH, SH, methyl, ethyl, F, Cl, and Br; wherein said complex is prepared according to a process hereof.

BRIEF DESCRIPTION OF THE DRAWINGS

The invention is illustrated by way of example and not limited by the accompanying figures.

DETAILED DESCRIPTION

Figure 1:
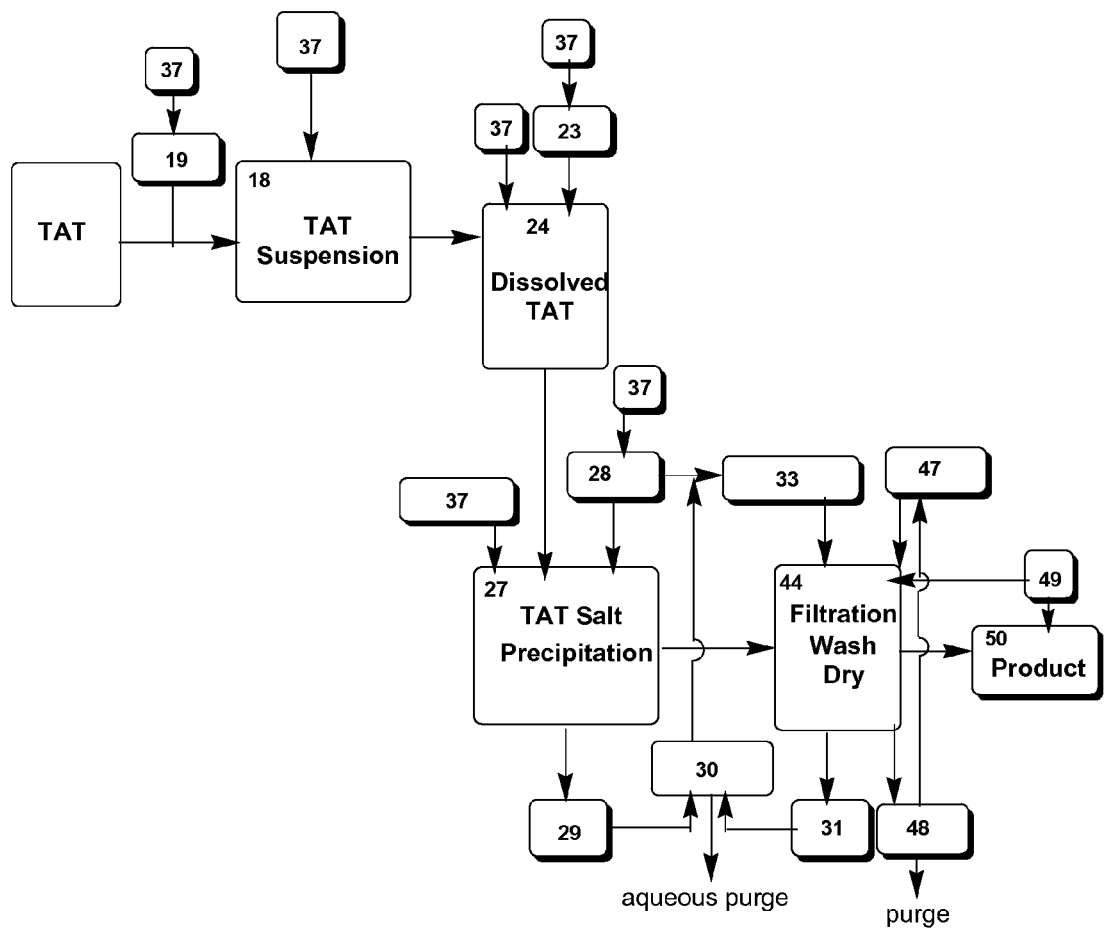
FIG. 1 is a schematic representation of an embodiment of the process described herein for the preparation of 2,3,5,6-tetraaminotoluene salt from 2,3,5,6-tetraaminotoluene in the presence of a reducing agent.

The following description is exemplary and explanatory only and is not restrictive of the invention, as defined in the appended claims.

In one embodiment, an aqueous mixture is provided comprising at least one 2,3,5,6-tetraaminotoluene species in suspension or in solution, and a reducing agent capable of reducing oxidation byproducts at the pH of the aqueous mixture.

In another embodiment, a process is provided for preparing 2,3,5,6-tetraaminotoluene salt, comprising: providing a 2,3,5,6-tetraaminotoluene feed in the form of an aqueous solution or aqueous suspension; contacting the 2,3,5,6-tetraaminotoluene source with an acid feed to form a reaction mixture at a temperature between about 10 and about 100° C. to produce 2,3,5,6-tetraaminotoluene salt; and cooling the reaction mixture to precipitate the 2,3,5,6-tetraaminotoluene salt; wherein at least one of: the 2,3,5,6-tetraaminotoluene feed, the acid feed and/or the reaction mixture further comprises a reducing agent; and wherein the reducing agent reduces oxidation byproducts at the pH of the feed and/or reaction mixture in which it is present.

In a further embodiment, a process is provided for preparing a complex of 2,3,5,6-tetraaminotoluene and the aromatic diacid XYTA, wherein the complex is generally described by Formula VI

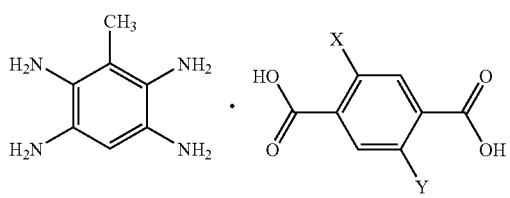

VI wherein X and Y are each independently selected from the group consisting of H, OH, SH, methyl, ethyl, F, Cl, and Br; comprising the sequential steps under exclusion of oxygen: providing a 2,3,5,6-tetraaminotoluene feed in the form of an aqueous solution or aqueous suspension; forming a reaction mixture by combining the 2,3,5,6-tetraaminotoluene feed with the following feeds:
 i. 0 to 5 equivalents of an acid
 ii. 0 to 5 equivalents of an organic base or an inorganic base;
 iii. optionally, a buffer solution; and
 iv. an XYTA source selected from XYTA and $M_2$XYTA (Formula VII)

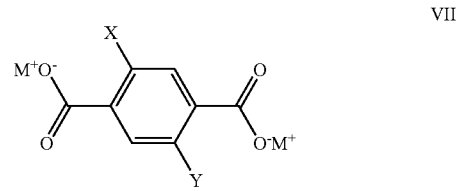

VII wherein M is K or Na, and wherein the molar ratio of XYTA to the 2,3,5,6-tetraaminotoluene salt is from 1:1 to 1:1.1; thereby adjusting the pH of the mixture to between about 3 and about 10 and thereby producing and precipitating the complex generally described by Formula (IV); and cooling, filtering, and washing the precipitated complex, wherein at least one of the feeds and/or the reaction mixture further comprises a reducing agent; and wherein the reducing agent reduces oxidation byproducts at the pH of the feed and/or reaction mixture in which it is present.

In the context of this disclosure, a number of terms shall be utilized.

As used herein, the term "aqueous mixture" includes mixtures containing water and mixtures containing both water and a co-solvent that is miscible with water.

As used herein, the term "oxidation byproducts" refers to substances produced by oxidation of a TAT species. Two examples of oxidation byproducts are 2-methyl-3,6-diiminocyclohexa-1,4-diene-1,4-diamine, phenazine-1,6-dimethyl-2,3,7,8-tetraamine, and phenazine-1,9-dimethyl-2,3,7,8-tetraamine.

As used herein, the term "TAT salt" or, equivalently, "2,3,5,6-tetraaminotoluene salt," denotes a compound formed by reaction of 2,3,5,6-tetraaminotoluene with an acid such as HCl, acetic acid, $H_2SO_4$, or $H_3PO_4$. One example of a TAT salt is TAT.4HCl.

As used herein, the term "XYTA" denotes 2-X-5-Y-terephthalic acid, where X and Y each independently selected from the group consisting of H, OH, SH, methyl, ethyl, F, Cl, and Br. One example is 2,5-dihydroxyterephthalic acid, "DHTA," in which X=Y=OH, The disodium or dipotassium salt of the diacid is represented by the term "$M_2$XYTA" where M is Na or K.

As used herein, the term "2,3,5,6-tetraaminotoluene species" includes 2,3,5,6-tetraaminotoluene, salts of 2,3,5,6-tetraaminotoluene (e.g., TAT.4HCl), and complexes of 2,3,5,6-tetraaminotoluene (e.g., TAT.DHTA).

As used herein, the term "net yield" of P denotes the actual, in-hand yield, i.e., the theoretical maximum yield minus losses incurred in the course of activities such as isolating, handling, drying, and the like.

As used herein, the term "purity" denotes what percentage of an in-hand, isolated sample is actually the specified substance.

In one embodiment, an aqueous mixture is provided comprising at least one tetraamine species in aqueous suspension or in aqueous solution, and a reducing agent wherein the reducing agent is capable of reducing oxidation byproducts at the pH of the aqueous mixture in which it is present.

Such reducing agents are effective at both eliminating and preventing formation of oxidation byproducts such as those described by Formulas II and III above. It is preferred that the reducing agents, when oxidized, do not react with any species present to form undesirable insoluble byproducts. Examples of suitable reducing agents for aqueous mixtures comprising at least one 2,3,5,6-tetraamine species and characterized by a pH less than 7 include but are not limited to Cr(II), Mn(II), Fe(0), Fe(II), Co(0), Co(II), Ni(0), Ni(II), Sn(0), Sn(II), Cu(0), Cu(I), Zn(0), Mg(0), and mixtures thereof. These reducing agents are typically used in the amount of at least 0.5 wt % and less than about 10 wt %, preferably less than about 5 wt %, and, more preferably, less than about 3 wt %. Examples of suitable reducing agents for aqueous mixtures comprising at least one 2,3,5,6-tetraamine species and characterized by a pH equal to or greater than 7 include but are not limited to $Na_2S_2O_4$, $Na_2SO_3$, $NaHSO_3$, $Na_2S_2O_5$, $(NH_4)_2SO_3H_2O$, hydroxylamine-O-sulfonic acid/KOH, hydrazines, hydroxylamines and salts thereof, aluminum, and mixtures thereof. These reducing agents are typically used in the amount of at least 0.5 wt % and less than about 10 wt %, preferably less than about 5 wt %, and, more preferably, less than about 3 wt %.

The aqueous mixture optionally comprises a miscible co-solvent. Examples of co-solvents include without limitation methanol, ethanol, and isopropanol.

In one embodiment, a process is provided for the preparation of 2,3,5,6-tetraaminotoluene salt ("TAT salt") from 2,3,5,6-tetraaminotoluene ("TAT") in the presence of a reducing agent, wherein the reducing agent is present in at least one feed and/or reaction mixture. All process steps are carried out under exclusion of oxygen. With reference to FIG. 1, an aqueous suspension feed 18 is prepared from TAT and deaerated water 19 containing about 5 to about 30 parts by weight of TAT in about 95 to about 70 parts deaerated water. About 1 to about 6 equivalents, preferably about 1 to about 3 equivalents, of an acid 23 are added to dissolve the TAT; as a result, a soluble salt of TAT is formed, herein referred to as "TAT salt." Any acid which allows for the dissolution of TAT in water and its subsequent re-precipitation is suitable. The selection of the acid depends on the specific needs and is based on solubility data and is easily done by one skilled in the art. Examples of suitable acids include without limitation HCl, acetic acid, $H_2SO_4$, and $H_3PO_4$. HCl is preferred, and the TAT salt generally prepared is TAT.4HCl. The solution may be heated to facilitate dissolution. Optionally, a co-solvent may be present. Examples of co-solvents include without limitation methanol, ethanol, and isopropanol. Optionally, the solution may be filtered through an absorbent material capable of absorbing impurities. Examples of absorbent materials include without limitation active carbon, alumina and microporous styrene.

Acid is then added 28 at a temperature in the range of about 10° C. to about 80° C. to form a reaction mixture from which the TAT salt 27 can be precipitated, for example, TAT.4HCl. The amount of acid needed for this step will depend on the concentration of TAT species in solution 24 and is readily determined by one skilled in the art. Typically, about 6 to about 8 equivalents of acid (as for example, 38% $HCl_{aq}$) are needed in this step to precipitate the TAT salt (for example, as TAT.4HCl) in about 90% yield. The use of gaseous acid, such as gaseous HCl, might reduce the total volume of liquid needed since the additional introduction of water with aqueous acid in both addition steps increases the absolute solubility of the TAT salt in the reaction mixture. The addition of equivalent amounts of acid in the gas phase instead of as an aqueous solution (for example, $HCl_{gas}$ instead of $HCl_{aq}$) is preferred since the liquid volumes are thereby reduced, and crystallization yields are expected to be higher as a consequence. Aqueous acid (for example, 30-38 wt % HCl) may be used because it is easier to handle than the acid in the gas phase. Aqueous acid can be recovered 29, distilled 30, and recycled (30, 28) or used in an acid wash step of the process (30, 33, 44).

The reaction mixture containing the precipitated TAT salt 27 is then cooled to about 5° C. to about 15° C. and stirred, then filtered. The TAT salt is then washed 44. It may be washed with deaerated aqueous acid, such as HCl (33%), and then optionally with deaerated ethanol or methanol to produce a wet cake material; the optional ethanol or methanol wash can then be recycled as shown in FIG. 1 48, 47 and a purge is drawn to prevent accumulation.

The resulting wet cake material (TAT salt) can be used in subsequent processing without drying or can be dried, as in FIG. 1 44, for example at a pressure less than 400 Torr and a temperature of about 30° C. to about 50° C., under a stream of $N_2$ 49. The dried product 50 is preferably kept under nitrogen.

Reducing agent 37 can be added to any or all of the feeds or reaction mixture that contain or are to be added to a TAT species, for example:

a. the water to be slurried with TAT to form the TAT suspension
b. the TAT suspension,
c. the acid to be used to dissolve the TAT
d. the TAT dissolved in acid, and
e. the reaction mixture from which the TAT salt is precipitated.

For example, as shown in the embodiment illustrated in FIG. 1, the reducing agent 37 can be added to one or more of the following feeds and/or reaction mixture: to the water 19 that will be used in forming the aqueous TAT suspension 18; to the aqueous suspension in a separate stream; to the acid 23 that will be used to dissolve the TAT; in a separate stream to the TAT after it has been dissolved in acid 24; to the acid 28 that is a component of the reaction mixture from which the TAT salt 27 is precipitated; or in a separate stream into the reaction mixture from which the TAT salt 27 is precipitated.

In a further embodiment, a process is provided for preparing a complex of 2,3,5,6-tetraaminotoluene and the aromatic diacid XYTA, wherein the complex is generally described by Formula VI

Figure 2:
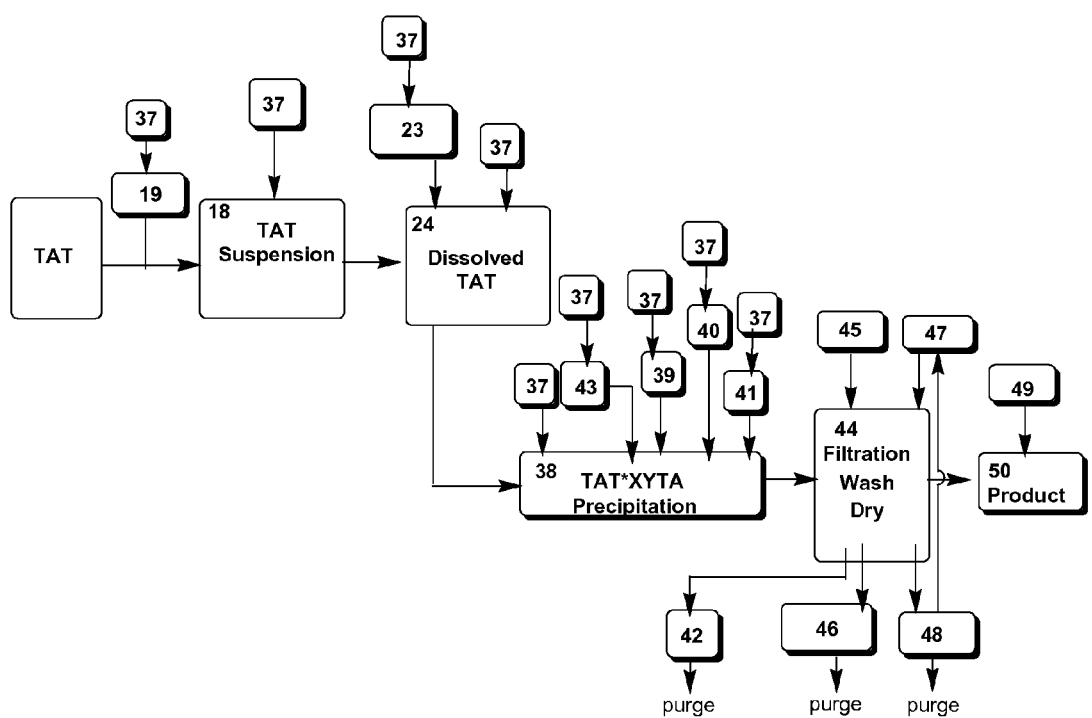
FIG. 2 is a schematic representation of an embodiment of the process described herein for the preparation of a complex of 2,3,5,6-tetraaminotoluene and the aromatic diacid XYTA in the presence of a reducing agent.

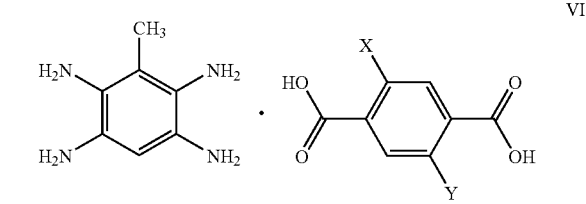

wherein X and Y are each independently selected from the group consisting of H, OH, SH, methyl, ethyl, F, Cl, and Br; wherein at least one reducing agent is present in at least one feed and/or reaction mixture. In a preferred embodiment, X and Y are each OH. All process steps are carried out under exclusion of oxygen. With reference to FIG. 2, an aqueous suspension feed 18 is prepared from TAT and deaerated water 19 containing about 5 to about 30 parts by weight of TAT in about 95 to about 70 parts deaerated water. About 1 to about 6 equivalents, preferably about 1 to about 3 equivalents, of an acid 23 are added to dissolve the TAT; as a result, a soluble salt of TAT is formed, herein referred to as "TAT salt."

Any acid which allows for the dissolution of TAT in water and its subsequent re-precipitation is suitable. The selection of the acid depends on the specific needs and is based on solubility data and is easily done by one skilled in the art. Examples of suitable acids include without limitation HCl, acetic acid, $H_2SO_4$, and $H_3PO_4$. HCl is preferred, and the TAT salt generally prepared is TAT.4HCl. The solution may be heated to facilitate dissolution. Optionally, a co-solvent may be present. Examples of co-solvents include without limitation methanol, ethanol, and isopropanol. Optionally the solution may be filtered through an absorbent material capable of absorbing impurities. Examples of absorbent materials include without limitation active carbon, alumina and microporous styrene.

The complex TAT.XYTA (Formula VI) is produced by combining the dissolved TAT 24 with about 0.5 to about 5 equivalents of a source of the XYTA moiety 39, thereby forming a reaction mixture 38. This is done under a nitrogen atmosphere 43 to exclude oxygen. The XYTA source can be the diacid XYTA, the salt $M_2XYTA$ (M=K or Na), or a mixture of XYTA and $M_2XYTA$. In a preferred embodiment, X and Y are each OH, and the XYTA source is the dipotassium salt of 2,5-dihydroxyterephthalic acid ("$K_2DHTA$"). The pH is adjusted to produce and precipitate the complex. The pH is adjusted to between about 3 and about 10, preferably between about 5 and about 8, i.e., the pH range at which the complex is least soluble, to precipitate the desired 1:1 complex and maximize yield. The pH is adjusted to the desired value using 0 to 5 equivalents of an acid; 0 to 5 equivalents of an organic base or an inorganic base; and, optionally, a buffer solution. Water may be used as well.

Examples of suitable acids include without limitation HCl, acetic acid, $H_2SO_4$, and $H_3PO_4$. Examples of suitable organic bases include without limitation aliphatic amines (for example, triethylamine) and carboxylates like acetate (acetate might need to be used in conjunction with a stronger base). Examples of suitable inorganic bases include without limitation KOH, NaOH, alkali carbonates, alkali bicarbonates, and ammonia. The acids and/or bases should not form undesirable products irreversibly when added to the reaction mixture. Also, any salt byproducts produced during complex formation should be readily removable (e.g., soluble in the reaction mixture or extractable with a solvent that does not dissolve the complex).

In the embodiment shown in FIG. 2, streams of water 40 and a basic solution 41 (for example, 2 equivalents NaOH) are added. The temperature of the mixture is initially about 40° C. to about 100° C., typically about 50° C. to about 60° C., and is gradually cooled to a temperature between about 5° C. to about 15° C. to promote complete precipitation of the complex. The preferred precipitation temperature will depend on the product concentration and on the amount of impurities present, but is generally chosen between about 0° and about 40° C., preferably between about 0° and about 20° C.

Various designs are possible for combining the dissolved TAT with the XYTA source and whatever acid, base, and/or buffer solutions are used to adjust the pH. FIG. 2 shows one embodiment in which a stream of TAT salt in an acid solution 34, the XYTA source 39, water 40, and base 41 are fed concurrently or consecutively into a vessel 38 wherein complex formation and precipitation take place. The XYTA source 39, water 40, and base 41 are most conveniently added as a single solution.

Reducing agent 37 can be added to any or all of the feeds or reaction mixture that contain or are to be added to a TAT species, for example:
  a. the water to be slurried with TAT to form the TAT suspension
  b. the TAT suspension,
  c. the acid to be used to dissolve the TAT
  d. the TAT dissolved in acid,
  e. the reaction mixture from which the TAT complex is precipitated,
  f. the XYTA source feed, and
  g. acidic, basic, and/or buffer solutions used to adjust the pH.

For example, as shown in the embodiment illustrated in FIG. 2, the reducing agent 37 can be added to one or more of the following feeds and/or reaction mixture: to the water 19 that will be used in forming the aqueous TAT suspension 18; to the aqueous suspension in a separate stream; to the acid 23 that will be used to dissolve the TAT; in a separate stream to the TAT after it has been dissolved in acid 24; to the XYTA source feed 39; to the water feed 40; and to the basic solution 41. Different reducing agents may be used in different streams in one process. For example, Sn(0) powder could be added to the acidic dissolved TAT solution 24, while $Na_2S_2O_4$ is added to a basic solution of the XYTA source 39 (e.g., $K_2DHTA$).

In other embodiments, TAT dissolved in an acid solution could be introduced into a vessel containing a basic XYTA source solution, or the XYTA source stream could be fed into the vessel containing the TAT dissolved in an acid solution. Alternatively, the XYTA source and TAT dissolved in an acid solution could be fed concurrently or consecutively into a buffer solution at the desired pH or into a basic solution to which an acid solution is subsequently added. Which design is best for a specific situation will be evident to one skilled in the art. In any of these variations, a reducing agent may be added directly to a stream or a vessel that contains a TAT species (for example, a vessel containing TAT dissolved in acid) or to a feed that will contact a TAT species (for example, a basic solution of XYTA source which will be added to a vessel containing TAT dissolved in acid).

Figure 3:
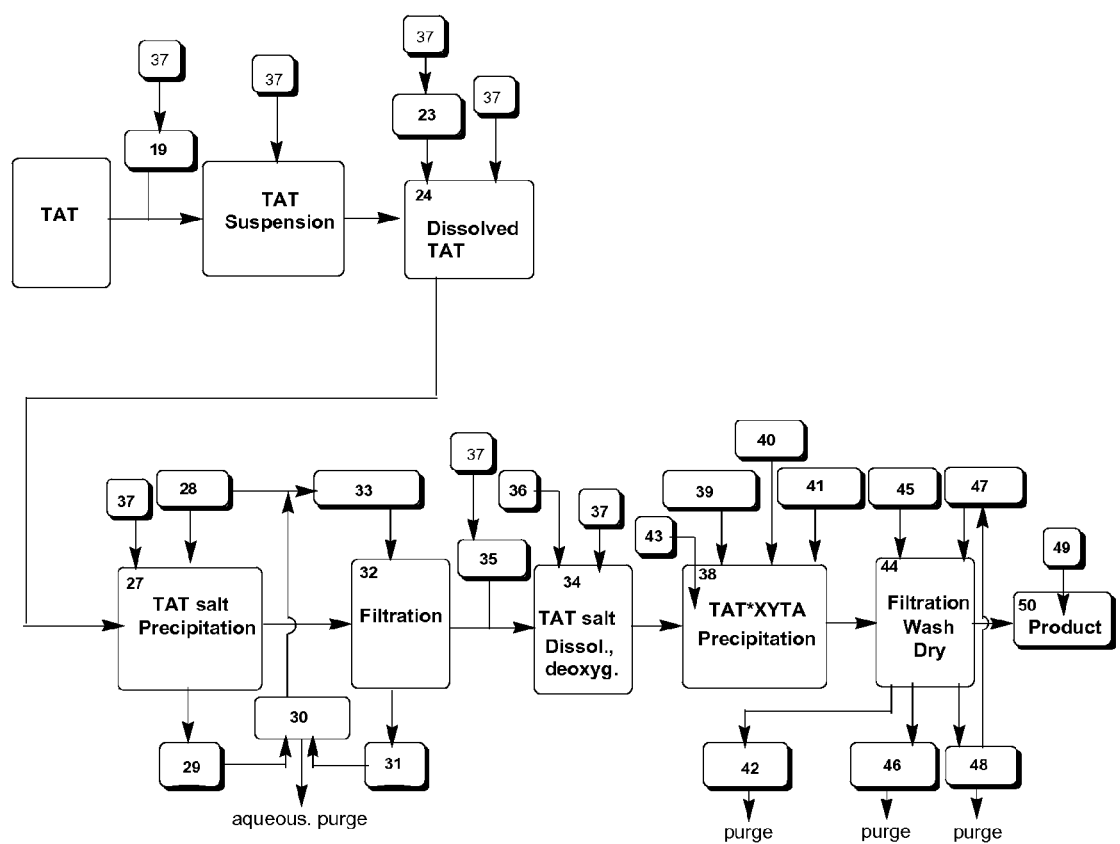
FIG. 3 is a schematic representation of another embodiment of the process described herein for the preparation of a complex of 2,3,5,6-tetraaminotoluene and the aromatic diacid XYTA in the presence of a reducing agent.

Another embodiment of a process for making TAT.XYTA complex, illustrated in FIG. 3, produces higher purity TAT.XYTA complex and allows for more flexibility in terms of production (timing) and easier dosage. An aqueous suspension feed 18 is prepared from TAT and deaerated water 19 containing about containing about 5 to about 30 parts by weight of TAT in about 95 to about 70 parts deaerated water. About 1 to about 6 equivalents, preferably about 1 to about 3 equivalents, of an acid 23 are added to dissolve the TAT; as a result, a soluble salt of TAT is formed, herein referred to as "TAT salt." Any acid which allows for the dissolution of TAT in water and its subsequent re-precipitation is suitable. The selection of the acid depends on the specific needs and is based on solubility data and is easily done by one skilled in the art.

Examples of suitable acids include without limitation HCl, acetic acid, $H_2SO_4$, and $H_3PO_4$. HCl is preferred, and the TAT salt generally prepared is TAT.4HCl. The solution may be heated to facilitate dissolution. Optionally, a co-solvent may be present. Examples of co-solvents include without limitation methanol, ethanol, and isopropanol. Optionally the solution may be filtered through an absorbent material capable of absorbing impurities. Examples of absorbent materials include without limitation active carbon, alumina and microporous styrene.

Acid is added 28 at a temperature in the range of about 10° C. to about 80° C. to form and precipitate the TAT salt 27, for example, TAT.4HCl. The amount of acid needed for this step will depend on the concentration of TAT in the filtrate and is readily determined by one skilled in the art. Typically, about 6 to about 8 equivalents of acid (as for example, 38% $HCl_{aq}$) are needed in this step to precipitate the TAT salt (for example, as TAT.4HCl) in about 90% yield. The use of gaseous acid, such as gaseous HCl, might reduce the total amount of acid needed since the additional introduction of water with aqueous acid in both addition steps increases the absolute solubility of the TAT salt in the filtered reaction mixture. The addition of equivalent amounts of acid in the gas phase instead of as an aqueous solution (for example, $HCl_{gas}$ instead of $HCl_{aq}$) is preferred since the liquid volumes are thereby reduced, and crystallization yields are expected to be higher as a consequence. Aqueous acid (for example, 30-38 wt % HCl) may be used because it is easier to handle than the acid in the gas phase. Aqueous acid can be recovered 29, distilled 30, and recycled (30, 28) or used in the acid wash step of the process (30, 33, 44).

The reaction mixture containing the precipitated TAT salt is then cooled to about 5° C. to about 15° C. and stirred, then filtered 32. Because the filtration step may have introduced small amounts of oxygen, nitrogen 36 is typically blown through it 34 in a deoxygenation step. The TAT salt is then washed with deaerated aqueous acid, such as concentrated HCl 33. The used aqueous acid can then be distilled and recycled (31, 30, 33). Water is added 35 to dissolve the washed TAT salt 34. Although filtration 32 and salt dissolution 34 are shown as occurring in separate vessels in the embodiment illustrated in FIG. 2, a single vessel could be used.

After the TAT salt is dissolved 34, the TAT.XYTA formation and precipitation, filtration, washing, and drying are carried out as described above (36 through 50).

In addition to the analogous possibilities illustrated by the embodiments shown in FIGS. 1 and 2, reducing agent 37 may be added to the water 35 used to dissolve the washed TAT salt and/or directly to the TAT salt solution 34.

The TAT.XYTA complex is recovered from the reaction mixture by filtration at a temperature in of the range of about 5° C. to about 50° C., preferably about 10° C. to about 15° C., and washed with water 45 and methanol 47, typically at a temperature in the range of about 15° C. to about 40° C. The methanol is recycled (47, 48) and a purge is drawn to prevent accumulation. Aqueous washes are discarded. In the embodiment shown in FIG. 1, there are two purge streams for aqueous wastes (42, 46), one of which (42) contains most of the oxidized reducing agent(s). The washed and dried TAT.XYTA complex 50 is kept under nitrogen 49 to protect it from oxygen. It is of high enough quality and purity to produce polybenzimidazole polymer of high enough molecular weight to make high performance fibers.

The materials, methods, and examples herein are illustrative only and, except as specifically stated, are not intended to be limiting.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

Materials.

The 2,3,5,6-tetraaminotoluene.4HCl was made from 2,6,-diamino-3,5-dinitrotoluene as described in Example 1 of copending U.S. Patent Application (CL4122) according to the following process: contacting 2,3,5,6-tetraaminotoluene with an aqueous solution comprising 1 to 6 equivalents of acid per mol of 2,3,5,6-tetraaminotoluene, optionally heating the solution, thereby dissolving the 2,3,5,6-tetraaminotoluene; forming and precipitating the 2,3,5,6-tetraaminotoluene salt by adding an acid to the dissolved 2,3,5,6-tetraaminotoluene, and washing the 2,3,5,6-tetraaminotoluene salt, wherein all steps are performed under oxygen exclusion.

The dipotassium salt of 2,5-dihydroxyterephthalic acid ("$K_2DHTA$") was made according to the method described in U.S. Pat. No. 6,040,478 (col. 3, lines 47-59). Its purity was between 98 and 99.8% with the major impurity potassium formate. The $K_2DHTA$ was dried to constant weight at 70° C. under vacuum to remove water.

Sodium hydroxide ("NaOH") was of 99% purity. Tin powder (99% purity) and iron powder (99% purity) were obtained from Sigma-Aldrich (Milwaukee, Wis., USA). All water used was deaerated and de-ionized water. The examples were carried out under exclusion of oxygen.

The meaning of abbreviations is as follows: "equiv" means equivalent(s), "g" means gram(s), "IV" means inherent viscosity, "L" means liter(s), "mg" means milligrams, "mL" means milliliter(s), "mmol" means millimole(s), "mol" means mole(s), "NMR" means nuclear magnetic resonance spectroscopy, "rpm" means revolutions per minute, and "UV" means ultraviolet spectroscopy.

Example 1

This Example demonstrates a larger-scale preparation of a high-purity complex of 2,3,5,6-tetraaminotoluene with 2,5-dihydroxyterephthalic acid dipotassium salt in the presence of Sn powder as a reducing agent.

TAT.4HCl (144.47 g, 0.485 mol, 1.1 equiv) was added to a 2 L bottle along with tin powder (0.78 g, 0.0066 mol, 0.015 equiv) and purged with nitrogen to ensure an inert atmosphere. To this vessel was added deaerated water (810 g). The solution was heated to 75° C. In a separate 1 L vessel, $K_2DHTA$ (120.88 g, 0.441 mol, 1 equiv) and NaOH (37.0 g, 0.925 mol, 2.1 equiv) were combined, purged thoroughly with nitrogen, dissolved in water (810 g) and heated to 50° C. The TAT.4HCl solution was added to the $K_2DHTA$/NaOH solution over 35 minutes which resulted in the formation of a flocculant light yellow precipitate. This mixture was then cooled to 25° C. over 90 minutes while being stirred. The light yellow solid was recovered by filtration, washed with water (80 mL) and methanol (80 mL), and was dried over two days under vacuum. This provided 147 g (95% net yield) of a light yellow solid.

NMR analysis indicated a 1.00:1.00 ratio of TAT to DHTA. Material was also polymerized using the following conditions: Total Mass: 15 g; TAT-DHTA complex (1.9 g); Solids: 10%; Tin powder: 9 mg; Polyphosphoric acid: 12.1 g and $P_2O_5$: 0.9 g. The mixture was mixed using an overhead mechanical stirrer and was subjected to the following temperature profile: 1 hour at 100° C.; 16 hours at 120° C. and 9 hours at 180° C. This gave a polymer with IV of 36.

Comparative Example A and Example 2 demonstrate how incorporation of a reducing agent (here, Sn) reduces the amount of deleterious impurities that are present in the complexation products.

Comparative Example A

TAT.4HCl (0.984 g, 3.300 mol, 1.1 equiv) that had been prepared without tin powder was added to a 40 mL vial. To this vial was added deaerated water (7.5 g). The solution was heated to 55° C. In a separate 20 mL vial, K$_2$DHTA (0.823 g, 3.00 mol, 1 equiv) and NaOH (0.252 g, 6.300 mmol, 2.1 equiv) were combined, purged thoroughly with nitrogen, dissolved in water (7.5 g) and heated to 55° C. The TAT.4HCl solution was added to the K$_2$DHTA/NaOH solution over 5 minutes which resulted in the formation of a flocculent light yellow precipitate. This mixture was then cooled to 25° C. over 60 minutes while being stirred. The resulting light pink solid was recovered by filtration, washed with water (5 mL) and methanol (5 mL), and was dried under vacuum for 60 minutes. This provided 0.847 g (81% net yield) of a pink solid.

NMR analysis indicated a 1.00:1.00 ratio of TAT to DHTA. The material was analyzed by $^1$H-NMR for oxidative decomposition products 3,6-diimino-2-methylcyclohexa-1,4-diene-1,4-diamine (Formula III), 1,6-dimethylphenazine-2,3,7,8-tetraamine (Formula IV), and 1,9-dimethylphenazine-2,3,7,8-tetraamine) (Formula V); amounts are presented in Table 1.

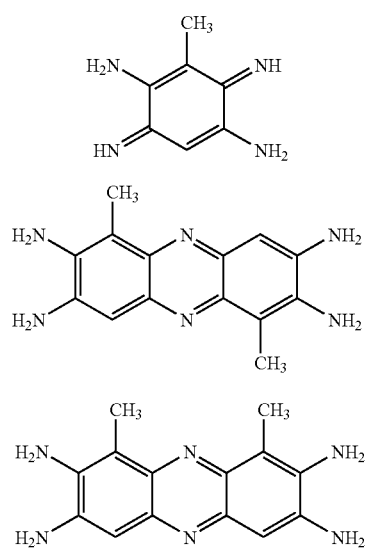

Example 2

TAT.4HCl (0.984 g, 3.300 mol, 1.1 equiv) that had been prepared with tin powder was added to a 40 mL vial. To this vial was added deaerated water (7.5 g). The solution was heated to 55° C. In a separate 20 mL vial, K$_2$DHTA (0.823 g, 3.00 mol, 1 equiv) and NaOH (0.252 g, 6.300 mmol, 2.1 equiv) were combined, purged thoroughly with nitrogen, dissolved in water (7.5 g) and heated to 55° C. The TAT.4HCl solution was added to the K$_2$DHTA/NaOH solution over 5 minutes which resulted in the formation of a flocculent light yellow precipitate. This mixture was then cooled to 25° C. over 60 minutes while being stirred. The resulting light pink solid was recovered by filtration, washed with water (5 mL) and methanol (5 mL), and was dried under vacuum for 60 minutes. This provided 0.919 g (88% net yield) of a pink solid.

NMR analysis indicated a 1.00:1.00 ratio of TAT to DHTA. The material was analyzed by $^1$H-NMR for oxidative decomposition products 3,6-diimino-2-methylcyclohexa-1,4-diene-1,4-diamine (Formula III), 1,6-dimethylphenazine-2,3,7,8-tetraamine (Formula IV), and 1,9-dimethylphenazine-2,3,7,8-tetraamine) (Formula V); amounts are presented in Table 1.

TABLE 1

| TAT·DHTA Complex Prep. Method | TAB:DHTA Ratio | % Yield (%) | Phenazines* (ppm) | Bis-imine** (ppm) |
|---|---|---|---|---|
| no tin | 1.00:1.00 | 81 | 1500 | 1700 |
| with tin | 1.00:1.00 | 88 | <100 | 0 |

*3,6-diimino-2-methylcyclohexa-1,4-diene-1,4-diamine (Formula III)
**1,6-dimethylphenazine-2,3,7,8-tetraamine (Formula IV) and 1,9-dimethylphenazine-2,3,7,8-tetraamine) (Formula V)

It is to be appreciated that certain features of the invention which are, for clarity, described above and below in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

Unless otherwise defined, all technical and scientific terms used herein have the same meaning as commonly understood by one of ordinary skill in the art to which this invention belongs. In case of conflict, the present specification, including definitions, will control.

Although methods and materials similar or equivalent to those described herein can be used in the practice or testing of the present invention, suitable methods and materials are described herein.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or end-point referred to.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless it is obvious that it is meant otherwise.

What is claimed is:

1. A process for preparing 2,3,5,6-tetraaminotoluene salt, comprising
   a) providing a 2,3,5,6-tetraaminotoluene feed in the form of an aqueous solution or an aqueous suspension;
   b) contacting the 2,3,5,6-tetraaminotoluene feed with an acid feed to form a reaction mixture at a temperature between about 10 and about 100° C. to produce 2,3,5,6-tetraaminotoluene salt; and
   c) cooling the reaction mixture to precipitate the 2,3,5,6-tetraaminotoluene salt;
wherein at least one of the feeds and/or the reaction mixture further comprises a reducing agent that reduces oxidation byproducts at the pH of the aqueous mixture.

2. The process of claim 1 wherein the reducing agent is selected from the group consisting of Cr(II), Mn(II), Fe(0). Fe(II), Co(0), Co(II), Ni(0), Ni(II), Sn(0), Sn(II), Cu(0), Cu(I), Zn(0), Mg(0), and mixtures thereof.

3. The process of claim 1 wherein the acid is selected from the group consisting of HCl, acetic acid, $H_2SO_4$, and $H_3PO_4$.

* * * * *